(12) United States Patent
Brown et al.

(10) Patent No.: US 6,384,991 B1
(45) Date of Patent: May 7, 2002

(54) PAIR OF GOGGLES WITH INCORPORATED MAGNIFYING GLASSES

(76) Inventors: Raymond Brown; Brenda Brown, both of 626 A Cedar Villa, Carrollton, GA (US) 30117

( * ) Notice: Subject to any disclaimer, the term of this patent is extended or adjusted under 35 U.S.C. 154(b) by 0 days.

(21) Appl. No.: 09/711,249

(22) Filed: Nov. 13, 2000

(51) Int. Cl.[7] .................................. G02B 7/02
(52) U.S. Cl. ....................... 359/815; 359/813
(58) Field of Search ..................... 359/802, 813, 359/815, 811; 2/195.1, 195.2, 195.3, 195.4; 345/8

(56) References Cited

U.S. PATENT DOCUMENTS

| | | | |
|---|---|---|---|
| 988,081 A | 3/1911 | Denman | 359/410 |
| 1,892,444 A | 12/1932 | Bausch | 359/409 |
| 2,024,322 A | 12/1935 | Wittig | 359/411 |
| 3,414,347 A | 12/1968 | Stolze | 359/480 |
| 3,572,931 A | * 3/1971 | Adler | 356/46 |
| 4,971,429 A | 11/1990 | Ishido et al. | 359/409 |
| 5,184,231 A | * 2/1993 | Ellis | 359/13 |
| 5,347,400 A | * 9/1994 | Hunter | 359/815 |

* cited by examiner

Primary Examiner—Ricky Mack
(74) Attorney, Agent, or Firm—Goldstein Law Offices, P.C.

(57) ABSTRACT

A pair of goggles with incorporated magnifying glasses including a face housing adapted for covering the eyes of a user. The face housing includes a top wall. The top wall has a forward edge and opposed side edges. The top wall has a pair of side walls extending downwardly from the opposed side edges thereof. The face housing includes an eye cover extending downwardly from the forward edge of the top wall. The eye cover includes a clear viewing area. An adjustable band is provided having opposed ends secured to the pair of side walls of the face housing for securement of the face housing to a head of the user. A pair of adjustable magnifying lenses are disposed within the clear viewing area of the eye cover of the face housing.

5 Claims, 2 Drawing Sheets

Fig. 2
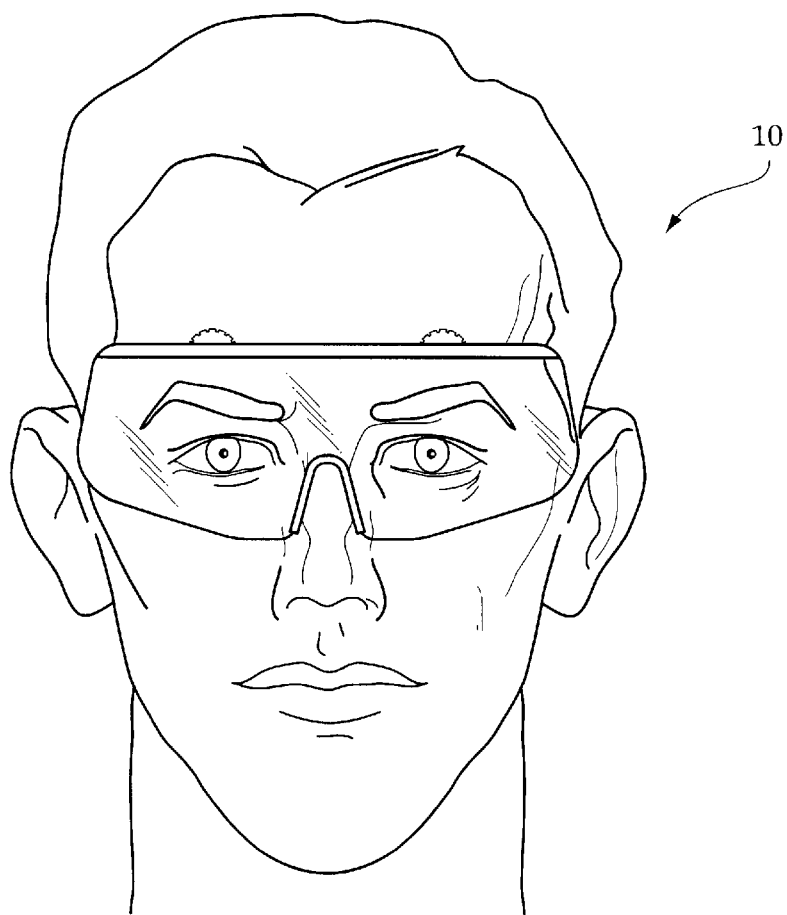
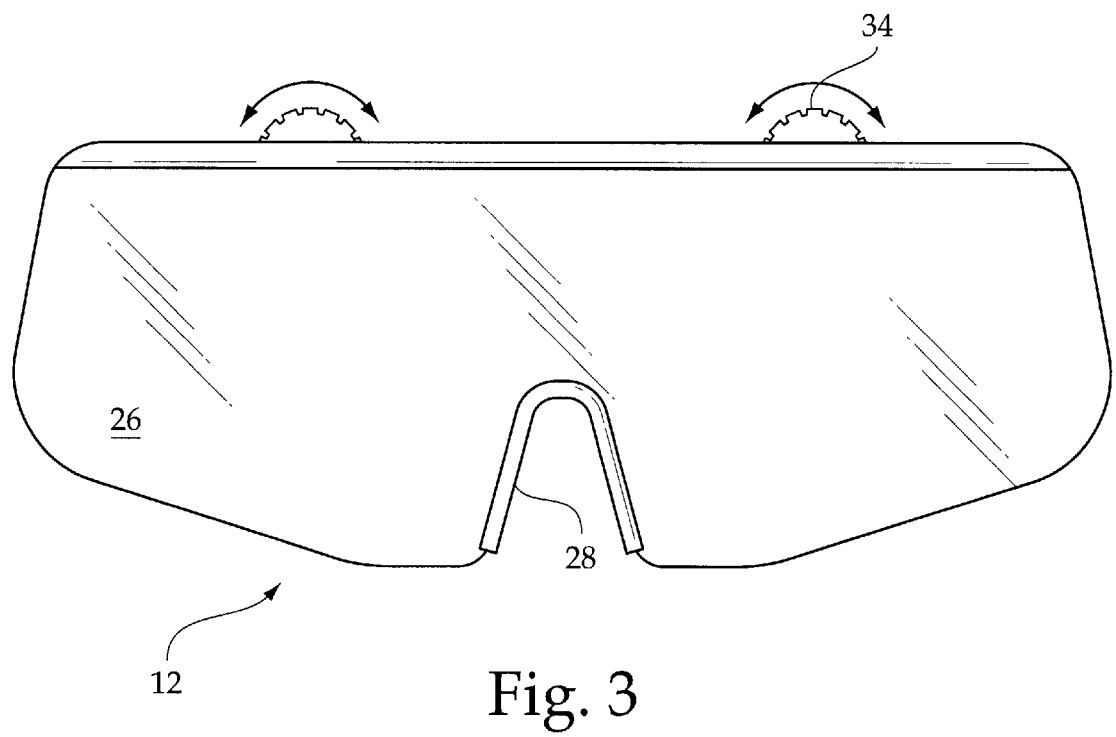
Fig. 3

PAIR OF GOGGLES WITH INCORPORATED MAGNIFYING GLASSES

BACKGROUND OF THE INVENTION

The present invention relates to a pair of goggles with incorporated magnifying glasses and more particularly pertains to allowing a person to adjustably magnify objects.

Typical attendees of sporting events and the like sometimes utilize binoculars to see the sporting event at a closer range. Standard binoculars require the user to hold them up to their eyes in order to look through them to increase the magnification of what they are viewing. The problem with this involves the tiring of the arm and wrist when holding the binoculars up for an extended period of time. What is needed is a device that can be used in a manner similar to binoculars while at the same time eliminating the need to hold the binoculars up to the user's face.

The present invention attempts to solve the abovementioned problem by providing a device that has the magnifying abilities of standard binoculars while also be able to be secured around the users head to allow for hands-free use.

The use of optical devices is known in the prior art. More specifically, optical devices heretofore devised and utilized for the purpose of enhancing vision are known to consist basically of familiar, expected and obvious structural configurations, notwithstanding the myriad of designs encompassed by the crowded prior art which have been developed for the fulfillment of countless objectives and requirements.

By way of example, U.S. Pat. No. 4,971,429 to Ishido discloses a pair of binoculars attached to the head of a user with a support band for hands free use. U.S. Pat. No. 3,414,347 to Stoltze discloses a binocular capable of providing magnified vision and mounting to the head of a user. U.S. Pat. No. 988,081 to Denman, U.S. Pat. No. 1,892,444 to Bausch, and U.S. Pat. No. 2,024,322 to Wittig disclose additional telescopic goggle devices.

While these devices fulfill their respective, particular objective and requirements, the aforementioned patents do not describe a pair of goggles with incorporated magnifying glasses for allowing a person to adjustably magnify objects.

In this respect, the pair of goggles with incorporated magnifying glasses according to the present invention substantially departs from the conventional concepts and designs of the prior art, and in doing so provides an apparatus primarily developed for the purpose of allowing a person to adjustably magnify objects.

Therefore, it can be appreciated that there exists a continuing need for a new and improved pair of goggles with incorporated magnifying glasses which can be used for allowing a person to adjustably magnify objects. In this regard, the present invention substantially fulfills this need.

SUMMARY OF THE INVENTION

In the view of the foregoing disadvantages inherent in the known types of optical devices now present in the prior art, the present invention provides an improved pair of goggles with incorporated magnifying glasses. As such, the general purpose of the present invention, which will be described subsequently in greater detail, is to provide a new and improved pair of goggles with incorporated magnifying glasses which has all the advantages of the prior art and none of the disadvantages.

To attain this, the present invention essentially comprises a face housing adapted for covering the eyes of a user. The face housing includes a top wall. The top wall has a forward edge and opposed side edges. The top wall has a pair of side walls extending downwardly from the opposed side edges thereof. The top wall has a pair of slots therethrough. The face housing includes an eye cover extending downwardly from the forward edge of the top wall. The eye cover includes a clear viewing area. The eye cover includes an upwardly extending nose recess. An adjustable band is provided having opposed ends secured to the pair of side walls of the face housing for securement of the face housing to a head of the user. A pair of adjustable magnifying lenses are disposed within the clear viewing area of the eye cover of the face housing. The lenses include adjustment dials disposed within the pair of slots of the top wall of the face housing.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved pair of goggles with incorporated magnifying glasses which has all the advantages of the prior art optical devices and none of the disadvantages.

It is another object of the present invention to provide a new and improved pair of goggles with incorporated magnifying glasses which may be easily and efficiently manufactured and marketed.

It is a further object of the present invention to provide a new and improved pair of goggles with incorporated magnifying glasses which is of durable and reliable construction.

An even further object of the present invention is to provide a new and improved pair of goggles with incorporated magnifying glasses which is susceptible of a low cost of manufacture with regard to both materials and labor, and which accordingly is then susceptible of low prices of sale to the consuming public, thereby making such a pair of goggles with incorporated magnifying glasses economically available to the buying public.

Even still another object of the present invention is to provide a new and improved pair of goggles with incorporated magnifying glasses for allowing a person to adjustably magnify objects.

Lastly, it is an object of the present invention to provide a new and improved pair of goggles with incorporated magnifying glasses including a face housing adapted for covering the eyes of a user. The face housing includes a top wall. The top wall has a forward edge and opposed side edges. The top wall has a pair of side walls extending downwardly from the opposed side edges thereof. The face housing includes an eye cover extending downwardly from the forward edge of the top wall. The eye cover includes a clear viewing area. An adjustable band is provided having opposed ends secured to the pair of side walls of the face housing for securement of the face housing to a head of the user. A pair of adjustable magnifying lenses are disposed within the clear viewing area of the eye cover of the face housing.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 2 is a front view of the present invention illustrated in place on a user.

FIG. 3 is an elevated front view of the present invention.

The same reference numerals refer to the same parts through the various figures.

DESCRIPTION OF THE PREFERRED EMBODIMENT

Figure 1:
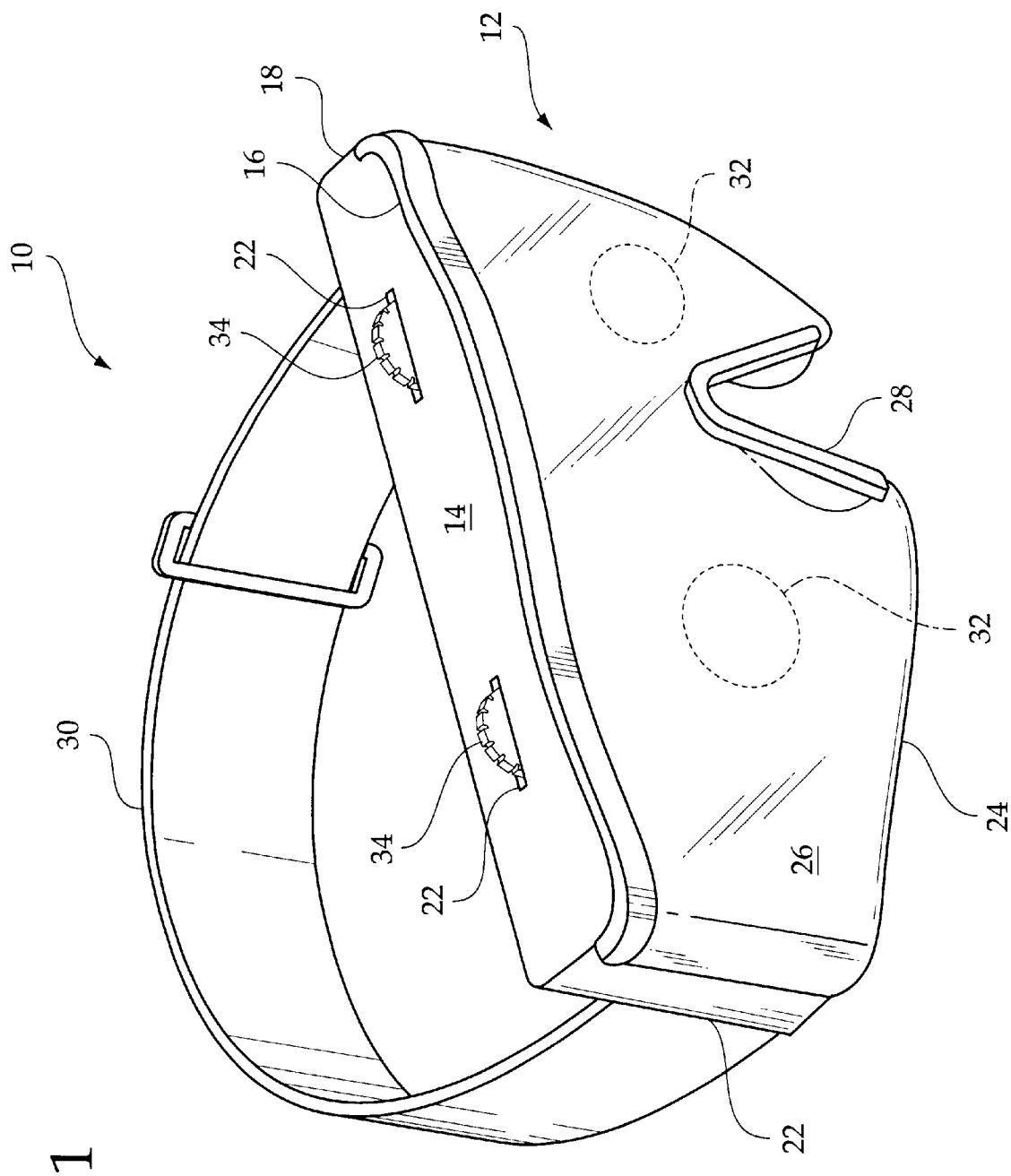
FIG. 1 is a perspective view of the preferred embodiment of the pair of goggles with incorporated magnifying glasses constructed in accordance with the principles of the present invention.

With reference now to the drawings, and in particular, to FIGS. 1 through 3 thereof, the preferred embodiment of the new and improved pair of goggles with incorporated magnifying glasses embodying the principles and concepts of the present invention and generally designated by the reference number 10 will be described.

Specifically, it will be noted in the various figures that the device relates to a pair of goggles with incorporated magnifying glasses for allowing a person to adjustably magnify objects. In its broadest context, the device consists of a face housing, an adjustable band, and a pair of adjustable magnifying lenses. Such components are individually configured and correlated with respect to each other so as to attain the desired objective.

The face housing 12 is adapted for covering the eyes of a user. The face housing 12 includes a top wall 14. The top wall 14 has a forward edge 16 and opposed side edges 18. The top wall 14 has a pair of side walls 20 extending downwardly from the opposed side edges 18 thereof. The top wall 14 has a pair of slots 22 therethrough. The face housing 12 includes an eye cover 24 extending downwardly from the forward edge 16 of the top wall 14. The eye cover 24 includes a clear viewing area 26. The eye cover 24 includes an upwardly extending nose recess 28. The nose recess 28 can be reinforced for comfort. The size of the face plate 12 can be varied to accommodate different users. Additionally, the face plate 12 can be somewhat flexible to allow it to conform to the unique shapes of the faces of individual users.

The adjustable band 30 has opposed ends secured to the pair of side walls 22 of the face housing 12 for securement of the face housing 12 to a head of the user.

The pair of adjustable magnifying lenses 32 are disposed within the clear viewing area 26 of the eye cover 24 of the face housing 12. The lenses 32 include adjustment dials 34 disposed within the pair of slots 22 of the top wall 14 of the face housing 12. The adjustment dials 34 can be rotated to bring the lenses 32 into proper focus.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A pair of goggles with incorporated magnifying glasses for allowing a person to adjustably magnify objects comprising, in combination:

a face housing adapted for covering the eyes of a user, the face housing including a top wall, the top wall having a forward edge and opposed side edges, the top wall having a pair of side walls extending downwardly from the opposed side edges thereof, the top wall having a pair of slots therethrough, the face housing including an eye cover extending downwardly from the forward edge of the top wall, the eye cover including a clear viewing area, the eye cover including an upwardly extending nose recess;

an adjustable band having opposed ends secured to the pair of side walls of the face housing for securement of the face housing to a head of the user; and a pair of adjustable magnifying lenses disposed within the clear viewing area of the eye cover of the face housing, the lenses including adjustment dials disposed within the pair of slots of the top wall of the face housing.

2. A pair of goggles with incorporated magnifying glasses for allowing a person to adjustably magnify objects comprising, in combination:

a face housing adapted for covering the eyes of a user, the face housing including a top wall, the top wall having a forward edge and opposed side edges, the top wall having a pair of side walls extending downwardly from the opposed side edges thereof, the face housing including an eye cover extending downwardly from the forward edge of the top wall, the eye cover including a clear viewing area;

an adjustable band having opposed ends secured to the pair of side walls of the face housing for securement of the face housing to a head of the user; and a pair of adjustable magnifying lenses disposed within the clear viewing area of the eye cover of the face housing.

3. The pair of goggles with incorporated magnifying glasses as set forth in claim 2, wherein the eye cover includes an upwardly extending nose recess.

4. The pair of goggles with incorporated magnifying glasses as set forth in claim 2, wherein the lenses include adjustment dials.

5. The pair of goggles with incorporated magnifying glasses as set forth in claim 4, wherein the adjustment dials are disposed within a pair of slots in the top wall of the face housing.

\* \* \* \* \*